US006310016B1

(12) United States Patent
Behal et al.

(10) Patent No.: US 6,310,016 B1
(45) Date of Patent: Oct. 30, 2001

(54) DETERGENT BAR COMPOSITION AND MANUFACTURING PROCESS COMPRISING COLLOIDAL ALUMINUM HYDROXIDE PHOSPHATE COMPLEX

(75) Inventors: Vidur Behal, Maharashtra; Atul Bhatia, Vadamangalam; Gurpreet Singh Kohli, Chakala, all of (IN); Mahesh Lakshminarayanan, Philadelphia, PA (US); Vineet Mital, Chakala (IN)

(73) Assignee: Unilever Home & Personal Care USA, Division of Conopco, Inc., Greenwich, CT (US)

( * ) Notice: Subject to any disclaimer, the term of this patent is extended or adjusted under 35 U.S.C. 154(b) by 0 days.

(21) Appl. No.: 09/730,136

(22) Filed: Dec. 5, 2000

(30) Foreign Application Priority Data

Dec. 8, 1999 (IN) ........................................ 902/BOM/99
Dec. 8, 1999 (IN) ........................................ 903/BOM/99

(51) Int. Cl.$^{7}$ ........................................ A61K 7/50
(52) U.S. Cl. ........................ 510/152; 510/141; 510/153; 510/155
(58) Field of Search ........................ 510/141, 152, 510/153, 155

(56) References Cited

U.S. PATENT DOCUMENTS 2,677,665 5/1954 James .
5,262,079 * 11/1993 Kacher et al. ........................ 252/108

FOREIGN PATENT DOCUMENTS

| | | |
|---|---|---|
| 307581 | 9/1918 | (DE) . |
| 0 825 252 | 2/1998 | (EP) . |
| 2234982 | 2/1991 | (GB) . |
| 2235205 | 2/1991 | (GB) . |
| 2235930 | 3/1991 | (GB) . |
| 2247463 | 3/1992 | (GB) . |
| 98/38280 | 9/1998 | (WO) . |
| 98/53040 | 11/1998 | (WO) . |
| 00/05333 | 2/2000 | (WO) . |
| 00/36075 | 6/2000 | (WO) . |

OTHER PUBLICATIONS

Search Report under Section 17, Application No. GB 00/02146.9 dated May 30, 2000.
International Search Report Application No. PCT/GB 00/04554 mailed Feb. 26, 2001.

* cited by examiner

*Primary Examiner*—Necholus Ogden
(74) *Attorney, Agent, or Firm*—Ronald A. Koatz

(57) ABSTRACT

A low total fatty matter detergent bar composition comprising 15–70% total fatty matter, 0.5–40% colloidal aluminium hydroxide-phosphate complex, and 10–50% water. The invention also comprises a process for making a bar of this composition comprising the steps of reacting a mixture of one or more fats or fatty acids with phosphoric acid and an alkaline aluminium-containing material to obtain an aluminium hydroxide-phosphate complex and soap at a temperature of 25–95° C.; adding water to the complex and soap mixture; and converting the product of (b) into bars.

13 Claims, No Drawings

DETERGENT BAR COMPOSITION AND MANUFACTURING PROCESS COMPRISING COLLOIDAL ALUMINUM HYDROXIDE PHOSPHATE COMPLEX

The invention relates to a synergistic composition of soap/detergent bars for personal and/or fabric washing. It also relates to a process for the preparation of such soap/detergent bars for personal and/or fabric washing. The invention particularly relates to a low total fatty matter (TFM) detergent bar comprising high levels of water and other liquid benefit agents, and a process for its manufacture.

Conventional detergent bars based on soap for personal washing usually contain over about 70% by weight total fatty matter (TFM), the remainder being water (about 10–20%) and other ingredients such as colour, perfume, preservatives, etc. Structurants and fillers are also present in such compositions in small amounts, which replace some of the soap in the bar while retaining the desired hardness of the bar. A few known fillers include starch, kaolin and talc.

Hard non-milled soap bars containing moisture of less than 35% are also available. These bars have a TFM of about 30–65%. The reduction in TFM has usually been achieved by the use of insoluble particulate materials and/or soluble silicates. Milled bars generally have a water content about 8–15%, and the hard non-milled bars have a water content of about 20–35%.

It is important to deliver sensory properties such as lather and skin feel, preferably by incorporating benefit agents in the formulation without altering the processability and physical properties of the bar. It is often found that it is a problem to formulate detergent compositions that would perform well under hard water conditions. Incorporation of builders such as phosphates or others in soap systems create problems such as efflorescence, gritty feel, etc.

IN 176384 discloses a detergent composition with low TFM content having high ratio of water to TFM without affecting hardness, cleaning and lathering properties of the bar by the incorporation of up to 20% colloidal aluminium hydroxide (A-gel). The A-gel/TFM combination enables the preparation of bars with higher water content while using TFM at a lower level. In this patent, although the A-gel concentration disclosed is up to 20% by weight, the demonstration of the invention is restricted to the use of 7.5% by weight A-gel in combination with 40% TEM with an additional structurant such as 5% by weight of alkaline silicate. IN 177828 discloses a process wherein by providing a balanced combination of aluminium hydroxide and TFM it is possible to prepare a low TFM bar having high water content but with satisfactory hardness. The patent teaches the generation of colloidal alumina hydrate in-situ by a reaction of fatty acid/fat with an aluminium containing alkaline material such as sodium aluminate to form bars which are obtained by plodding. Our co-pending application 811/Bom/98 (corresponding to GB 9906834.8) discloses that use of A-gel from 9 to 16% by weight of the composition synergistically improves the processability, sensory and physical properties of low TFM bars.

In addition, our co-pending application 810/Bom/98 (corresponding to WO/EP99/09042) discloses a process of preparing a low TFM bar utilising a reaction of fatty acid with an aluminium containing alkaline material such as sodium aluminate solution that specifically has a solid content of 20 to 55%, wherein the alumina ($Al_2O_3$) to sodium oxide ($Na_2O$) is in a ratio of 0.5 to 1.55 by weight that gives superior bar properties. These bars have improved hardness and smoother feel. This reaction can take place in a broader temperature range of 40 to 95° C.

In the process of the invention, it has now been found that in situ generation of aluminium hydroxide-phosphate complex by a reaction of fatty acid/fat in presence of phosphoric acid with an aluminium containing alkaline material such as sodium aluminate solution that preferably has a solid content of 20 to 55%, preferably wherein the alumina ($Al_2O_3$) to sodium oxide ($Na_2O$) is in a ratio of 0.5 to 1.55 by weight gives superior bar properties. These bars will have significantly lower density and improved physical properties such as bar hardness without interfering with the sensory properties. By this process it is possible to formulate bars that are suitable for both soft and hard water situations.

It is an advantage of the invention to be able to formulate detergent compositions suitable for both soft and hard water situations where the density, processability and physical properties such as hardness of the bar are improved significantly by incorporation of colloidal aluminium hydroxide phosphate complex (Alphos).

It is another advantage of the invention to be able to manufacture extruded detergent bars using fatty acids mixtures having an Iodine Value (IV) in the range from.0 to 110. It is particularly significant that using fatty acid mixtures with an IV beyond 70 and the incorporation of Alphos as a structurant it is possible to produce detergent bars with good physical properties by an extrusion route, without the addition of processing aids such as silicates. It has also been possible to structure better and higher levels of liquid benefit agents other than water by the incorporation of colloidal aluminium hydroxide phosphate complex (Alphos).

According to a first aspect of the invention there is provided a low TFM detergent bar composition comprising from 15 to 70% by weight of total fatty matter;

from 0.5 to 40% by weight of colloidal aluminium hydroxide-phosphate complex (e.g. Alphos);

from 10 to 55% by weight of water; and optionally other benefit agents;

the balance being other and minor additives

According to a preferred aspect of this invention there is provided a low TFM detergent bar composition comprising from 15 to 70% by weight of total fatty matter;

from 0.5 to 40% by weight of colloidal aluminium hydroxide-phosphate complex (e.g. Alphos);

from 10 to 55% by weight of water;

from 5–60% benefit agents;

the balance being other and minor additives.

According to a further aspect, there is provided process for preparing a low TFM detergent bar composition comprising:

from 15 to 70% by weight of total fatty matter;

from 0.5 to 40% by weight of colloidal aluminium hydroxide-phosphate complex (e.g. Alphos);

from 10 to 55% by weight of water; and optionally other benefit agents;

the balance being other and minor additives as herein described, which process comprises the steps of:

a. reacting a mixture of one or more fatty acids/fat such as herein described and phosphoric acid with an aluminium containing alkaline material such as sodium aluminate with a solid content of e.g. 20 to 55% wherein the $Al_2O_3$ to $Na_2O$ is e.g. in a ratio of 0.5 to 1.55 by weight to obtain a mixture of aluminium hydroxide-phosphate complex and soap at a temperature between 25° C. to 95° C.;

b. adding predetermined amount of water to the mixture of aluminium hydroxide-phosphate complex and soap;

c. adding if desired, other and minor additives such as herein described to the mixture of step (b)

d. converting the product of step (c) into bars by conventional method.

In the process of the invention, it is. especially preferable to maintain a weight ratio of $Al_2O_3$ to phosphoric acid in the range 0.40 to 2.40:1. The phosphoric acid used in the reaction is preferably 26–85% pure. The particle size of aluminium hydroxide-phosphate complex may range from 0.1 to 25 $\mu$m.

The process of the invention is carried out in any mixer conventionally used in soap/detergent manufacture and is preferably a high shear kneading mixer. The preferred mixers include a ploughshare mixer, mixers with kneading members of Sigma type, multi-wiping overlap, single curve or double arm. The double arm kneading mixers can be of overlapping or the tangential design. Alternatively the invention can be carried out in a helical screw agitator vessel or multi-head dosing pump/high shear mixer and spray drier combinations as in conventional processing.

The term total fatty matter, usually abbreviated to TFM is used to denote the percentage by weight of fatty acid and triglyceride residues present without taking into account the accompanying cations.

For a soap having 18 carbon atoms, an accompanying sodium cation will generally amount to about 8% by weight. Other cations may be employed as desired, for example zinc, potassium, magnesium, alkyl ammonium and aluminium.

The term soap denotes salts of carboxylic fatty acids. The soap may be derived from any of the triglycerides conventionally used in soap manufacture—consequently the carboxylate anions in the soap may contain from 8 to 22 carbon atoms.

The soap may be obtained by saponifying a fat and/or a fatty acid. The fats or oils generally used in soap manufacture may be such as tallow, tallow stearines, palm oil, palm stearines, soya bean oil, fish oil, caster oil, rice bran oil, sunflower oil, coconut oil, babassu oil, palm kernel oil, and others. In the above process the fatty acids are derived from oils/fats selected from coconut, rice bran, groundnut, tallow, palm, palm kernel, cotton seed, soybean, castor etc. The fatty acid soaps can also be synthetically prepared (e.g. by the oxidation of petroleum or by the hydrogenation of carbon monoxide by the Fischer-Tropsch process). Resin acids, such as those present in tall oil, may be used. Naphthenic acids are also suitable.

Tallow fatty acids can be derived from various animal sources and generally comprise about 1–8% myristic acid, about 21–32% palmitic acid, about 14–31% stearic acid, about 0–4% palmitoleic acid, about 36–50% oleic acid and about 0–5% linoleic acid. A typical distribution is 2.5% myristic acid, 29% palmitic acid, 23% stearic acid, 2% palmitoleic acid, 41.5% oleic acid, and 3% linoleic acid. Other similar mixtures, such as those from palm oil and those derived from various animal tallow and lard are also included.

Coconut oil refers to fatty acid mixtures having an approximate carbon chain length distribution of 8% $C_8$, 7% $C_{10}$, 48% $C_{12}$, 17% $C_{14}$, 8% $C_{16}$, 2% $C_{18}$, 7% oleic and 2% linoleic acids (the first six fatty acids listed being saturated). Other sources having similar carbon chain length distributions, such as palm kernel oil and babassu kernel oil, are included within the term coconut oil.

According to a preferred aspect of the invention up to 60% benefit agents such as non-soap surfactants, skin benefit materials such as moisturisers, emollients, sunscreens, or anti-ageing compounds are incorporated at any step prior to step of milling. Alternatively certain of these benefit agents are introduced as macro domains during plodding.

A typical suitable fatty acid blend consists of 5 to 30% coconut fatty acids and 70 to 95% fatty acids ex-hardened rice bran oil. Fatty acids derived from other suitable oils/fats such as groundnut, soybean, tallow, palm, palm kernel, etc. may also be used in other desired proportions.

For the purpose of the invention the colloidal aluminium hydroxide phosphate complex may be prepared by reacting aluminium containing alkaline material such as sodium aluminate with a solid content of 20 to 55% wherein the $Al_2O_3$ to $Na_2O$ is in a ratio of 0.5 to 1.55, preferably 1.0 to 1.5, with phosphoric acid at a temperature range of 25 to 95° C. It is especially preferable to maintain a weight ratio of $Al_2O_3$ to phosphoric acid in the range 0.40 to 2.40. The commercially available phosphoric acid used is preferably 26–85% pure.

The non-soap surfactants may be anionic, nonionic, cationic, amphoteric or zwitterionic, or a mixture thereof. Examples of moisturisers and humectants include polyols, glycerol, cetyl alcohol, carbopol 934, ethoxylated castor oil, paraffin oils, lanolin and its derivatives. Silicone compounds such as silicone surfactants like DC3225C (Dow Corning) and/or silicone emollients, or silicone oil (DC-200 Ex-Dow Corning) may also be included. Suitable sun-screens include 4-tertiary butyl-4'-methoxy dibenzoylmethane (available under the trade name PARSOL 1789 from Givaudan) and/or 2-ethyl hexyl methoxy cinnamate (available under the trade name PARSOL MCX from Givaudan) or other UV-A and UV-B sun-screens.

Other additives such as one or more water insoluble particulate materials such as talc, kaolin, polysaccharides such as starch or modified starches and celluloses may be incorporated.

In step (c) of the process minor additives such as perfume, colour, preservatives and other conventional additives at 1 to 2% by weight can be incorporated.

The composition according to the invention will preferably comprise detergent actives which are generally chosen from both anionic and nonionic detergent actives.

Suitable anionic detergent active compounds are water soluble salts of organic sulphuric reaction products having in the molecular structure an alkyl radical containing from 8 to 22 carbon atoms, and a radical chosen from sulphonic acid or sulphuric acid ester radicals and mixtures thereof.

Examples of suitable anionic detergents are sodium and potassium alcohol sulphates, especially those obtained by sulphating the higher alcohols produced by reducing the glycerides of tallow or coconut oil; sodium and potassium alkyl benzene sulphonates such as those in which the alkyl group contains from 9 to 15 carbon atoms; sodium alkyl glyceryl ether sulphates, especially those ethers of the higher alcohols derived from tallow and coconut oil; sodium coconut oil fatty acid monoglyceride sulphates; sodium and potassium salts of sulphuric acid esters of the reaction product of one mole of a higher fatty alcohol and from 1 to 6 moles of ethylene oxide; sodium and potassium salts of alkyl phenol ethylene oxide ether sulphate with from 1 to 8 units of ethylene oxide molecule and in which the alkyl radicals contain from 4 to 14 carbon atoms; the reaction product of fatty acids esterified with isethionic acid and neutralised with sodium hydroxide where, for example, the fatty acids are derived from coconut oil and mixtures thereof.

The preferred water-soluble synthetic anionic detergent active compounds are the alkali metal (such as sodium and potassium) and alkaline earth metal (such as calcium and magnesium) salts of higher alkyl benzene sulphonates and mixtures with olefin sulphonates and higher alkyl sulphates, and the higher fatty acid monoglyceride sulphates.

Suitable nonionic detergent active compounds can be broadly described as compounds produced by the condensation of alkylene oxide groups, which are hydrophilic in nature, with an organic hydrophobic compound which may be aliphatic or alkyl aromatic in nature. The length of the hydrophilic or polyoxyalkylene radical which is condensed with any particular hydrophobic group can be readily adjusted to yield a water-soluble compound having the desired degree of balance between hydrophilic and hydrophobic elements.

Particular examples include the condensation product of aliphatic alcohols having from 8 to 22 carbon atoms in either straight or branched chain configuration with ethylene oxide, such as a coconut oil ethylene oxide condensate having from 2 to 15 moles of ethylene oxide per mole of coconut alcohol; condensates of alkylphenols whose alkyl group contains from 6 to 12 carbon atoms with 5 to 25 moles of ethylene oxide per mole of alkylphenol; condensates of the reaction product of ethylenediamine and propylene oxide with ethylene oxide, the condensate containing from 40 to 80% of polyoxyethylene radicals by weight and having a molecular weight of from 5,000 to 11,000; tertiary amine oxides of structure $R_3NO$, where one group R is an alkyl group of 8 to 18 carbon atoms and the others are each methyl, ethyl or hydroxyethyl groups, for instance dimethyldodecylamine oxide; tertiary phosphine oxides of structure $R_3PO$, where one group R is an alkyl group of from 10 to 18 carbon atoms, and the others are each alkyl or hydroxyalkyl groups of 1 to 3 carbon atoms, for instance dimethyldodecylphosphine oxide; and dialkyl sulphoxides of structure $R_2SO$ where the group R is an alkyl group of from 10 to 18 carbon atoms and the other is methyl or ethyl, for instance methyltetradecyl sulphoxide; fatty acid alkylolamides; alkylene oxide condensates of fatty acid alkylolamides and alkyl mercaptans.

It is also possible to include cationic, amphoteric, or zwitterionic detergent actives in the compositions according to the invention.

Suitable cationic detergent actives that can be incorporated are alkyl substituted quaternary ammonium halide salts e.g. bis (hydrogenated tallow) dimethylammonium chlorides, cetyltrimethyl ammonium bromide, benzalkonium chlorides and dodecylmethylpolyoxyethylene ammonium chloride and amine and imidazoline salts for e.g. primary, secondary and tertiary amine hydrochlorides and imidazoline hydrochlorides.

Suitable amphoteric detergent-active compounds that optionally can be employed are derivatives of aliphatic secondary and tertiary amines containing an alkyl group of 8 to 18 carbon atoms and an aliphatic radical substituted by an anionic water-solubilizing group, for instance sodium 3-dodecylamino-propionate, sodium 3-dodecylaminopropane sulphonate and sodium N-2-hydroxydodecyl-N-methyltaurate.

Suitable zwitterionic detergent-active compounds that optionally can be employed are derivatives of aliphatic quaternary ammonium, sulphonium and phosphonium compounds having an aliphatic radical of from 8 to 18 carbon atoms and an aliphatic radical substituted by an anionic water-solubilising group, for instance 3-(N-N-dimethyl-N-hexadecylammonium) propane-1-sulphonate betaine, 3-(dodecylmethyl sulphonium) propane-1-sulphonate betaine and 3-(cetylmethylphosphonium) ethane sulphonate betaine.

The invention will now be further described by way of illustration only, with reference to the following non-limiting examples which amongst other things show comparative results of the composition prepared by the present invention and beyond the invention.

EXAMPLES

Examples 1–7

Preparation of the Soap Bars

Soap base prepared by the conventional route was mixed with structurants such as talc (Example 1) or A-gel+talc (Example 2) or colloidal aluminium hydroxide phosphate complex (Alphos, Example 3) prepared separately in a high shear mixer by reacting aluminium containing alkaline material such as sodium aluminate with a solid content of 40% wherein the $Al_2O_3$ to $Na_2O$ is in a ratio of 1.1 with 85% phosphoric acid at a temperature of 80° C. The minor and other ingredients were added and mixed. The bars were extruded by the conventional process. The formulation of the bars are presented in Table 1.

The samples prepared as described above were tested for hardness (penetration value) and density by the following procedure.

Penetration Value (PV)

Penetration value indicating the hardness of the bar was measured using a cone penetrometer; the details of a typical instrument and the method of measurement is given below.

Cone type Penetrometer

MANUFACTURER: Adair Dutt & Company, Bombay.

RANGE OF MEASUREMENT: 0–40 mm

RANGE OF VERIFICATION: 20 in steps of 5

Procedure of Measurement: Let the entire mass (comprised of penetrometer needle and standard weight) which just rests on the test sample drop freely and thus penetrate the test mass to a specific distance for a specified period of time and read this distance to the nearest $1/10^{th}$ mm. Take the average after repeating the exercise for at least 3 times.

Density of the Bar

The density of the bar is measured by the standard method and calculated using the formula:

$$\text{Density (grams/cm}^3\text{)} = \frac{\text{Weight of bar (grams)}}{\text{Volume in cm}^3}$$

TABLE 1

| | Example 1 | Example 2 | Example 3 |
|---|---|---|---|
| Soap | 44.5 | 44.5 | 45.5 |
| Liquid benefit agent viz. AOS | 4 | 4 | 4 |
| Free Moisture | 12.5 | 12.5 | 12.5 |
| Structurant (37%) | Talc | A-gel + talc | Alphos |
| Minors | 2 | 2 | 2 |
| Product Characteristics | | | |
| Density | 1.362 | 1.346 | 1.224 |
| Penetration Value (mm) | 32.4 | 28.8 | 11.5 |

The data presented in Table 1 shows that using Alphos as a structuring aid it is possible to obtain lower density bars with improved hardness.

Incorporation of Liquid Benefit Agents

The formulations presented in Table 2 were prepared as described above, but higher levels of liquid benefit agents were incorporated. The hardness of the bars was tested by the procedure described above using a penetrometer.

TABLE 2

| | Example 4 | Example 5 | Example 6 | Example 7 |
|---|---|---|---|---|
| Soap | 44.5 | 44.5 | 44.5 | 44.5 |
| Liquid benefiting agent viz. AOS (1) | 9 | 11 | 7 | 7 |
| Alphos | 32 | 30 | — | — |
| A-gel + Talc | — | — | 34 | — |
| Moisture | 12.5 | 12.5 | 12.5 | 12.5 |
| Talc | — | — | — | 34 |
| Minor | 2 | 2 | 2 | 2 |
| Product Characterisitic | | | | |
| Penetration Value | 25 | 21.6 | >70, Not processable | >70, Not processable |

(1) Alpha olefin sulphonate

The data presented in Table 2 shows that it is possible to incorporate higher levels of liquid benefit agents when the bars are structured using Alphos. Using the conventional structuring system it is not possible to incorporate liquid benefit agents at levels >7%. Incorporation of non-soap detergent actives improves the lather, feel and other in use properties while being milder on skin. Another important benefit of Alphos as a structuring system is that the formulation performance is good both under hard and soft water conditions.

Examples 8–9

Process for Preparing the Soap Bar a. Process According to Prior Art (Example 8) A batch of soap was prepared by melting a mixture of fatty acids at 80–85° C. in a crutcher and neutralising with 40% sodium aluminate solution. The sodium aluminate solution was prepared by dissolving solid alumina trihydrate in sodium hydroxide solution at 90–95° C. Additional water was added to obtain the moisture content of about 36% in the crutcher. The soap mass was spray dried to the required moisture, under vacuum and formed into noodles. The soap noodles were mixed with talc, perfume, colour, titanium dioxide in a sigma mixer and passed twice through a triple roll mill. The milled chips were plodded under vacuum and formed into billets. The billets were cut and stamped into tablets.

b. Process According to the Invention (Example 9)

A batch of soap was prepared by adding a mixture of melted fatty acids at 80–85° C. and phosphoric acid in a ratio of TFM:phosphoric acid of 6.66 in a high shear mixer, and neutralising with 40% sodium aluminate solution. The resulting mass was mixed with minors, perfume, colour and titanium dioxide in a sigma mixer, and passed twice through a triple roll mill. The milled chips were plodded under vacuum and formed into billets. The billets were cut and stamped into tablets.

The samples prepared as described above were tested for hardness (penetration value) as described in relation to Example 1 above, and feel (grittiness) by the following procedure.

Feel

A standard washing procedure in cold water is followed for estimation of grittiness of feel by a group of trained panellists. The score is given over scale of 1–10, where score of 1 relates to the best feel and 10 to the poorest. The toilet soaps with acceptable quality generally have a feel score in the range of 7.0 to 8.3.

TABLE 1

| Composition % wt. | Example 8 | Example 9 |
|---|---|---|
| Soap | 44.5 | 44.5 |
| Liquid benefit agent viz. AOS | 4 | 4 |
| Structurant (37%) (equivalent levels) | A-gel (8%) + talc (29%) | Alphos |
| Moisture | 12.5 | 12.5 |
| Minors | 2 | 2 |
| Product Characteristics | | |
| Penetration Value | 28.8 | 11.5 |
| Feel | 7.6 | 7.6 |

The data presented shows that at similar similar soap and moisture contents, bars according to the invention with Alphos results in harder product, while delivering equivalent sensorial feel. It is not possible to increase the A-gel level beyond 8% in the above composition, and hence the hardness of the bar can not be improved further using such structurants.

What is claimed is:

1. A low total fatty matter detergent bar composition comprising 15–70% total fatty matter, 0.5–40% colloidal aluminium hydroxide-phosphate complex, and 10–50% water.

2. A bar according to claim 1, wherein the composition additionally comprises 5–60% benefit agents.

3. A bar according to claim 1, wherein the composition has an iodine value in the range 0 to 110.

4. A bar according to claim 1, wherein the colloidal aluminium hydroxide-phosphate complex is prepared from an aluminium containing alkaline material.

5. A bar according to claim 4, wherein the aluminium containing alkaline material is sodium aluminate with a solid content of 20–55% and an $Al_2O_3$ to $Na_2O$ ratio of 0.5 to 1.55:1.

6. A bar according to claim 5, wherein the aluminium containing alkaline material is mixed with phosphoric acid at a temperature in the range of 25–95° C.

7. A process for preparing a low total fatty acid detergent bar comprising 15–70% total fatty matter, 0.5–40% colloidal aluminium hydroxide-phosphate complex and 10–55% water, comprising the steps of:

a. reacting a mixture of one or more fats or fatty acids with phosphoric acid and an alkaline aluminium-containing material to obtain an aluminium hydroxide-phosphate complex and soap at a temperature of 25–95° C.;

b. adding water to the complex and soap mixture;

c. converting the product of (b) into bars.

8. A process according to claim 7, wherein the aluminium containing alkaline material is sodium aluminate.

9. A process according to claim 7, wherein the sodium aluminate has a solids content of 20 to 55%.

10. A process according to claim 7, wherein the $Al_2O_3$ to $Na_2O$ ratio is in the region 0.5 to 1.55:1.

11. A process according to claim 7, wherein the particle size of the aluminium hydroxide-phosphate complex is 0.1–25 $\mu$m.

12. A process according to claim 7, wherein the process is carried out in a high sheer kneading mixer.

13. A process according to claim 7, wherein the ratio of $Al_2O_3$ to phosphoric acid is in the ratio 0.4 to 2.4:1.

* * * * *